United States Patent
Yu et al.

(10) Patent No.: US 12,048,715 B2
(45) Date of Patent: Jul. 30, 2024

(54) CIS-PLATINUM CROSS-LINKED PROTEIN HYDROGEL AND PREPARATION METHOD THEREOF

(71) Applicant: Hangzhou Normal University, Hangzhou (CN)

(72) Inventors: Shuangjiang Yu, Hangzhou (CN); An Yan, Hangzhou (CN); Shu Wei, Hangzhou (CN); Hongcheng Sun, Hangzhou (CN); Junqiu Liu, Hangzhou (CN)

(73) Assignee: Hangzhou Normal University, Hangzhou (CN)

( * ) Notice: Subject to any disclaimer, the term of this patent is extended or adjusted under 35 U.S.C. 154(b) by 0 days.

(21) Appl. No.: 18/458,057

(22) Filed: Aug. 29, 2023

(65) Prior Publication Data
US 2023/0398143 A1   Dec. 14, 2023

Related U.S. Application Data

(63) Continuation of application No. PCT/CN2022/089407, filed on Apr. 26, 2022.

(30) Foreign Application Priority Data

Oct. 28, 2021   (CN) .......................... 202111279597.4

(51) Int. Cl.
  A61K 33/243   (2019.01)
  A61K 9/06    (2006.01)
  A61K 47/42   (2017.01)

(52) U.S. Cl.
  CPC .............. A61K 33/243 (2019.01); A61K 9/06 (2013.01); A61K 47/42 (2013.01)

(58) Field of Classification Search
  CPC ........ A61K 33/243; A61K 9/06; A61K 47/42; A61K 47/643; A61K 45/06; A61P 35/00; Y02A 50/30
  See application file for complete search history.

(56) References Cited

U.S. PATENT DOCUMENTS

| | | | |
|---|---|---|---|
| 4,584,392 A | 4/1986 | Smith et al. | |
| 6,077,545 A | 6/2000 | Roskos et al. | |

FOREIGN PATENT DOCUMENTS

| | | |
|---|---|---|
| CN | 109528627 A | 3/2019 |
| CN | 111621038 A | 9/2020 |
| CN | 112451473 A | 3/2021 |
| CN | 112451542 A | 3/2021 |
| WO | 2020151727 A1 | 7/2020 |
| WO | WO-2020151727 A1 * 7/2020 ........... A61K 31/282 |

OTHER PUBLICATIONS

Internation Search Report of PCT/CN2022/089407, Mailed Aug. 3, 2022.
Zhong, Yanqiang et al., "Study on the Preparation Technology of Cisplatin Albumin Microspheres", Academic Journal of Second Military Medical University, vol. 19, No. 3, Jun. 30, 1998, ISSN:2097-1338, pp. 286-287.
Liang, Jun et al., "Controlled release of BSA-linked cisplatin through a PepGel self-assembling peptide nanofiber hydrogel scaffold.", Amino Acids, vol. 49, No. 12, Jun. 12, 2017, ISSN:1438-2199, pp. 2015-2021.
Zhang, Zhen, "Click-type Cross-linking Strategy to Prepare Hydrogels for Drug Delivery and Tissue Adhesive", Chinese Doctoral Dissertations Full-text Database, Engineering Sciences I, No. 1, Jan. 15, 2021, ISSN:1674-022X, document No. B014-476.
Zhang, Yi et al., "Self-Stabilized Hyaluronate Nanogel for Intracellular Codelivery of Doxorubicin and Cisplatin to Osteosarcoma.", Advanced Science, vol. 5, No. 5, May 31, 2018, ISSN:2198-3844, document No. 1700821.
Li, Rongchang et al., "Interactions between Bovine Serum Albumin (BSA) with Tetrachloroplatinate(II), Cisplatin and Cis-diaquodiammineplatin(II)", Chinese Journal of Inorganic Chemistry, vol. 6, No. 3, Sep. 30, 1990, ISSN:1001-4861, pp. 339-343.

* cited by examiner

*Primary Examiner* — Ali Soroush

(57) ABSTRACT

Disclosed are a cis-platinum cross-linked protein hydrogel and a preparation method thereof. Main components of the cis-platinum cross-linked protein hydrogel comprise the following ingredients in percentage by mass: 0.5% to 5.0% drug, 6.0% to 50.0% serum albumin and 47.0% to 93.0% solvent medium; a carboxyl group on a surface of the serum albumin and the drug form a coordinate bond; and the drug is cis-platinum. A hydrogel preparation is simple in structure and easy to prepare, and the used cis-platinum has dual effects: a cross-linking agent for promoting the formation of protein hydrogels and an antitumor drug for exerting a tumor inhibition curative effect. The strategy simplifies the carrier design and reduces potential toxic side effects. The protein carboxyl limits the release of cis-platinum through a coordination effect so that reduce the burst release of the loaded drugs drastically.

6 Claims, 3 Drawing Sheets

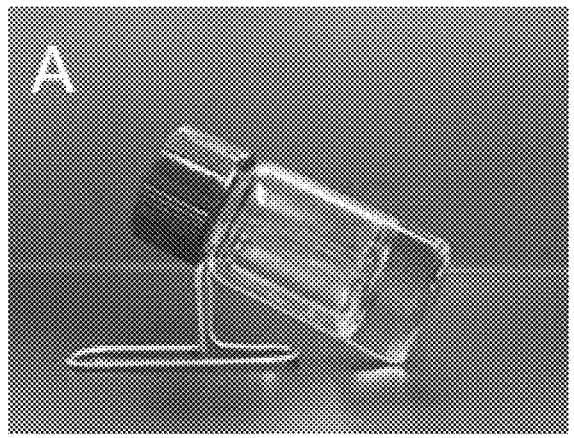
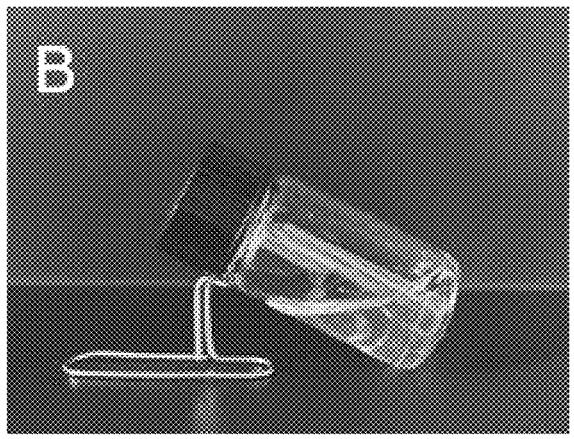
FIG. 1A  FIG. 1B
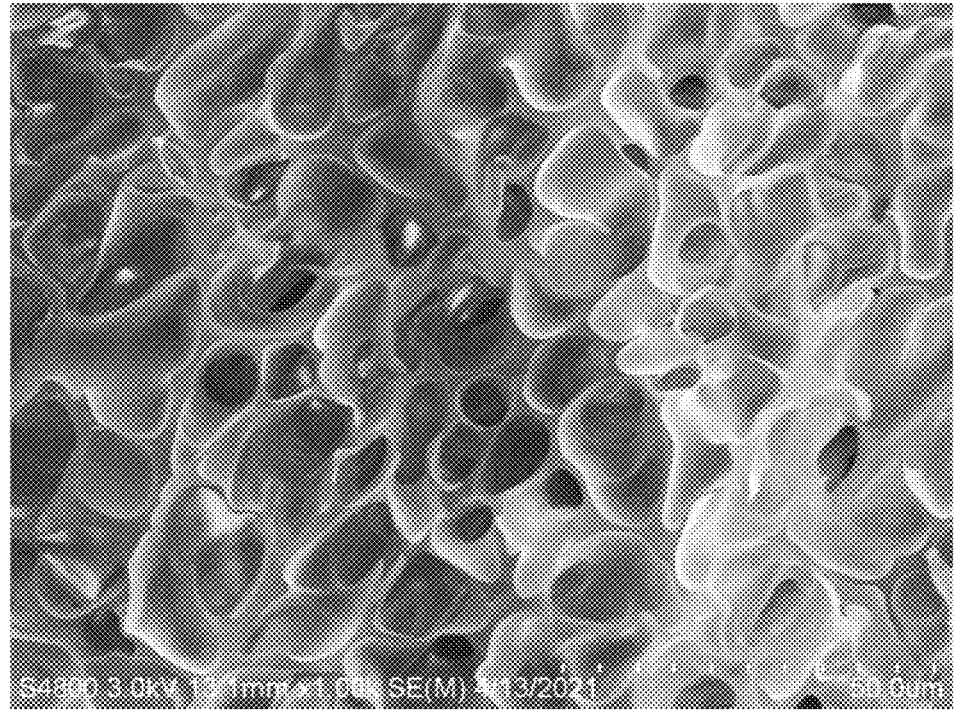
FIG. 2

CIS-PLATINUM CROSS-LINKED PROTEIN HYDROGEL AND PREPARATION METHOD THEREOF

CROSS-REFERENCE TO RELATED APPLICATIONS

This application is a continuation of International Patent Application No. PCT/CN2022/089407 with a filing date of Apr. 26, 2022, designating the United States, now pending, and further claims priority to Chinese Patent Application No. 202111279597.4 with a filing date of Oct. 28, 2021. The content of the aforementioned applications, including any intervening amendments thereto, are incorporated herein by reference.

TECHNICAL FIELD

The present invention belongs to the field of pharmaceutical preparations and particularly relates to a cis-platinum cross-linked protein hydrogel and a preparation method thereof.

BACKGROUND OF THE PRESENT INVENTION

A major challenge when treating cancer is elevating chemotherapy efficacy and reducing the side effects of toxic drugs. Although the intravenous administration method has been widely used in clinic, the disadvantages of serious side effects and low effective drug concentration are in focus. Local tumor treatment has the advantages of concentrated drug administration and small systemic side effects and can overcome physiological administration obstacles, so local tumor treatment has been widely studied and studied in recent years.

A hydrogel is a material with a three-dimensional network structure and contains a large amount of water or biological fluids. According to different sources of components, hydrogels may be divided into two categories: natural polymer hydrogels and synthetic polymer hydrogels. Natural polymers mainly comprise polysaccharides (such as chitosan and hyaluronic acid) and proteins (such as collagen, gelatin and albumin), and synthetic polymers mainly comprise materials of polymethacrylic acid and derivatives thereof, polyester, polyether and polyamino acid. In different types of hydrogels, the use of natural protein as a base of gel material has many advantages, such as good biocompatibility, adjustable viscoelasticity and in vivo biodegradability, and has broad application prospects in drug delivery, biosensing, tissue engineering and artificial organs. Albumin is the most important protein in body serum, has the characteristics of easy availability, easy solubility and good biocompatibility and is widely used in the biomedical field.

The hydrogel, as a drug carrier, can be locally used as a drug release repository, which can continuously provide an effective drug concentration to the focus parts in time and deliver the drug to the focus parts more directly in space. This method is more direct and effective than systemic treatment, especially for drugs with greater toxicity and side effects; thus, it is a very promising administration method. However, for water-soluble drugs (such as cis-platinum and doxorubicin hydrochloride), an early drug burst release behavior is a problem that cannot be ignored and can greatly weaken the regulatory effect of the hydrogel carrier, thus affecting the therapeutic effect. Moreover, drugs with early burst release will cause larger local side toxicity. Therefore, it is necessary to reduce the burst release behavior of drugs and realize the controllability of drug release to give full play to the advantages of hydrogel carriers.

A cis-platinum drug is a conventional chemotherapy drug that has the characteristics of a broad anticancer spectrum and definite curative effect and is used in the clinical treatment of various solid tumors. However, due to the side effects, the cis-platinum drug often causes great psychological and physical harm to patients. If local sustained-release treatment with this drug can be realized, there are good potential application values for reducing the side effects of systemic treatment of patients, improving the quality of life of patients and improving the tumor compression of patients with late-stage cancers.

SUMMARY OF PRESENT INVENTION

One object of the present invention is to provide a protein prodrug hydrogel preparation with a cis-platinum drug as a cross-linking agent and a preparation method thereof aiming at the defects in the prior art.

The present invention provides a cis-platinum cross-linked protein hydrogel, wherein main components of the cis-platinum cross-linked protein hydrogel comprise the following ingredients in percentage by mass: 0.5% to 5.0% drug, 6.0% to 50.0% serum albumin and 47.0% to 93.0% solvent medium; a carboxyl group on a surface of the serum albumin and the drug form a coordinate bond;
  the drug is cis-platinum;
  the serum albumin is one of human serum albumin, bovine serum albumin and mouse serum albumin; and
  the solvent medium is water or a solution without chloride ions.

Preferably, a percentage by mass of the serum albumin is 15.0% to 40.0%, and most preferably 20.0% to 30.0%.

Preferably, a percentage by mass of the drug is 1.5% to 2.0%.

Another objective of the present invention is to provide a preparation method of the cis-platinum cross-linked protein hydrogel, which specifically comprises the following steps:
  step (1): preparing the serum albumin and the solvent medium into a serum protein solution at a certain concentration, and heating the solution in a water bath at 25° C. to 65° C. for a period of time until albumin is completely dissolved to obtain a clear protein solution; and
  step (2): adding drug to the clear protein solution, and a coordination reaction was carried out between the drug and a carboxyl group on the surface of the serum albumin in the solvent medium at a certain temperature to produce a cis-platinum complex; and then placing the complex on a shaking table at a constant temperature of 4° C. to 65° C. under a rotating speed of 10 r/min to 230 r/min for a period of time to obtain the cis-platinum cross-linked protein hydrogel.

Preferably, the coordination reaction is carried out at a temperature of 10° C. to 50° C.

However, another objective of the present invention is to provide an application of the cis-platinum cross-linked protein hydrogel in a sustained-release carrier.

However, another objective of the present invention is to provide a combined drug, which comprises the cis-platinum cross-linked protein hydrogel and other drugs loaded on the cis-platinum cross-linked protein hydrogel.

Preferably, the other drug may be an immune adjuvant agent or an immune checkpoint blockade antibody.

It can be seen from a rheological experiment and a degradation experiment that the cis-platinum cross-linked protein gel has good in vitro stability but can be degraded under stimulation by protease and chloride ions, thus achieving sustained drug release. It can be seen from the data of a cell experiment that compared with a pure cis-platinum drug, the cis-platinum cross-linked albumin hydrogel has obviously reduced toxicity in a short period, which proves that the hydrogel has an obvious sustained release effect on the drug. This is caused by a coordination effect between the carboxyl on the surface of the albumin and the cis-platinum, and this property is of great significance for reducing side effects caused by the burst release behavior of the drug and prolonging the action time of the drug in tumor parts.

The cis-platinum cross-linked albumin hydrogel obtained by the present invention has a characteristic of triggering degradation by chloride ions and good biocompatibility and biodegradability, which is beneficial for further application of the hydrogel as a drug carrier in vivo. The products obtained by degradation are only serum albumin and cis-platinum, wherein the former may be absorbed or decomposed by the body and is basically harmless to the human body, while the latter may be used as a chemotherapy drug to enter tumor cells to play an antitumor role; therefore, the hydrogel has broad application prospects.

Compared with the prior art, the hydrogel preparation provided by the present invention is simple in structure and easy to prepare, and the used cis-platinum has dual effects: a cross-linking agent for promoting formation of protein hydrogel and an antitumor drug for playing a tumor inhibition curative effect. According to the present invention, the introduction of other components is effectively reduced, and the potential risk of body side effects is reduced. On the other hand, protein carboxyl limits the release of cis-platinum through a coordination effect so that the burst release behavior of the drug can be reduced to a great extent, and the reduction in the toxicity of cis-platinum in body tissue is facilitated, thus providing an effective solution for improving local tumor treatment efficiency.

DESCRIPTION OF THE DRAWINGS

FIG. 1A is a photo showing gel formation of a cis-platinum cross-linked protein hydrogel obtained in Embodiment 1;

FIG. 1B is a photo showing that cross-linked gel formation is failed when a percentage by mass of a drug is less than 0.5%;

FIG. 2 is an SEM microstructural diagram of the cis-platinum cross-linked protein hydrogel obtained in Embodiment 1;

DETAILED DESCRIPTION OF PREFERRED EMBODIMENTS

Figure 3:
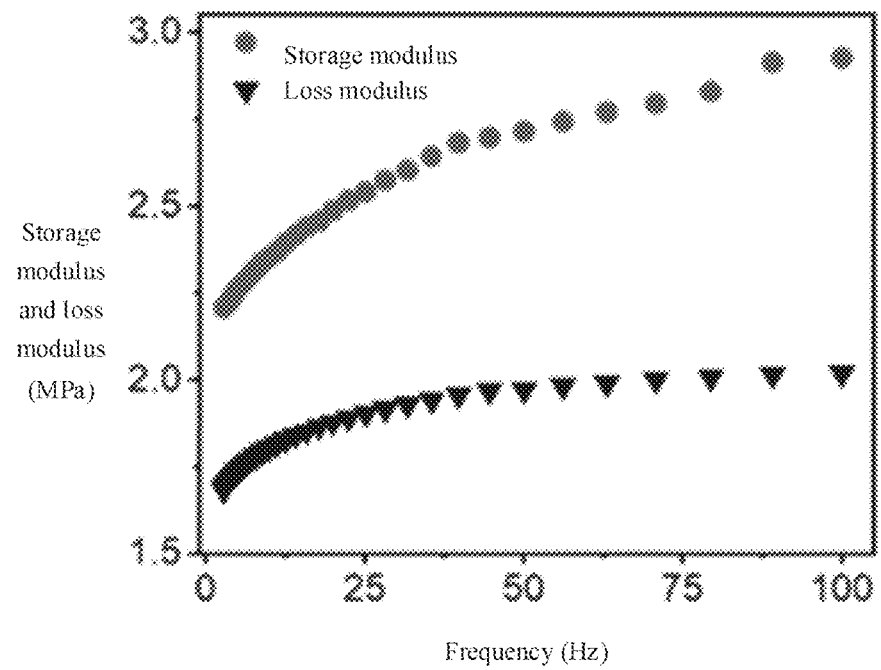
FIG. 3 shows a rheological property of the cis-platinum cross-linked protein hydrogel obtained in Embodiment 1.

To further understand the present invention, preferred implementations of the present invention will be described hereinafter with reference to embodiments, but it should be understood that these descriptions are only for further explaining the features and advantages of the present invention and are not intended to limit the claims of the present invention.

The present invention provides a protein hydrogel with a cis-platinum drug as a cross-linking agent, which comprises the cis-platinum drug, serum albumin and a solvent medium. A percentage by mass of the serum albumin in a gel material is preferably 6.0% to 50.0%, more preferably 15.0% to 40.0%, and most preferably 20.0% to 30.0%. A content of the cis-platinum drug is preferably 0.5% to 5.0%, more preferably 1.0% to 3.0%, and most preferably 1.5% to 2.0%.

According to the present invention, a drug-loading hydrogel preparation is prepared with the cis-platinum drug, which contains the serum albumin and the solvent as described in the technical solution above.

The drug loaded gel preparation prepared by the present invention may be prepared into a serum protein solution at a certain concentration through the solvent medium and added with the cis-platinum drug to obtain a drug-loading cis-platinum crosslinked hydrogel by controlling conditions.

Preferably, the solvent medium is ultrapure water and any solution without chloride ions, and the solution must have a functional group that forms a coordination effect with platinum atoms. The percentage by mass of the serum albumin in the gel material is preferably 6.0% to 50.0%, more preferably 15.0% to 40.0%, and most preferably 20.0% to 30.0%.

Meanwhile, the serum protein solution in the gel material can not only be cross-linked with cis-platinum for local treatment but also be cross-linked with other antitumor drugs capable of forming a coordinate bond with carboxyl groups. The hydrogel may be used separately or in combination with other drugs (such as a protein polypeptide drug, an immune adjuvant and an immune checkpoint blockade antibody). It should be said that the chloride ion responsive hydrogel material is a universal drug loading platform for local disease treatment, and a drug type, a degradation time, an indication and the like can be adjusted according to needs.

To further illustrate the present invention, the cis-platinum cross-linked albumin hydrogel and the preparation method thereof provided by the present invention are described in detail with reference to the embodiments.

Embodiment 1

First, 300 mg of bovine serum albumin powder was added to 700 µL of ultrapure water and heated in a water bath at 45° C. for complete dissolution to obtain a clear light yellow solution. 15 mg of cis-platinum was added to the solution and placed on a shaking table, wherein the temperature was set to 42° C. and the rotating speed was set to 230 r/min, or the cis-platinum was evenly dispersed in the solution by mechanical stirring. After reaction for 36 hours to 48 hours, a protein hydrogel with cis-platinum as a cross-linking agent was obtained.

The cis-platinum cross-linked albumin hydrogel prepared in Embodiment 1 of the present invention was quickly frozen by a liquid nitrogen quick freezing method, and a freeze-dried gel sample was obtained by freeze-drying. The sample was subjected to a scanning electron microscope test to obtain a microscopic photo of the gel. It can be seen from FIG. 2 that a complex hydrogel material has a connected macroporous structure, which is beneficial for transporting and releasing a drug in the gel material.

FIG. 1(A) is a photo showing gel formation of the cis-platinum cross-linked protein hydrogel obtained in Embodiment 1.

FIG. 1(B) is a photo showing that cross-linked gel formation is failed when a percentage by mass of the drug is less than 0.5%.

FIG. 3 shows a rheological study result of the cis-platinum cross-linked protein hydrogel obtained in Embodiment 1.

Embodiment 2

200 mg of bovine serum albumin powder was added to 800 μL of ultrapure water and heated in a water bath at 45° C. for complete dissolution to obtain a clear light yellow solution. 15 mg of cis-platinum was added to the solution and placed on a shaking table, wherein the temperature was set to 10° C. and the rotating speed was set to 230 r/min, or the cis-platinum was evenly dispersed in the solution by mechanical stirring. After reaction for 72 hours to 84 hours, a protein hydrogel with cis-platinum as a cross-linking agent was obtained.

In the process of preparing the cis-platinum cross-linked albumin hydrogel in Embodiment 2 of the present invention, a colloid with fluidity was poured from a container into a mold with a bottom diameter of 2.5 cm when the cis-platinum completely disappeared and put into a shaking table, wherein the temperature was set to 45° C. so that gel formation was continued. After gel formation, a disc-shaped gel was removed and placed on a rotary rheometer to test the modulus of the cis-platinum cross-linked albumin hydrogel.

Figure 4:
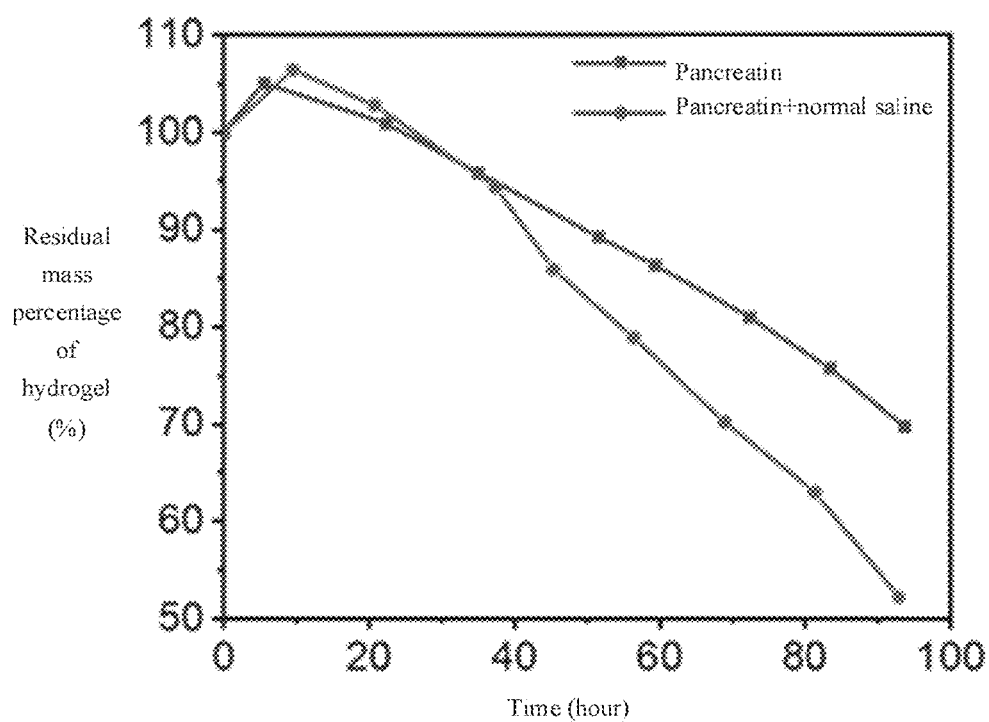
FIG. 4 shows an in vitro degradation experimental result of a cis-platinum cross-linked protein hydrogel obtained in Embodiment 2.

A trypsin solution with a physiological condition concentration and a normal saline solution with a physiological condition concentration were added into the cis-platinum cross-linked albumin hydrogel prepared in Embodiment 2 and cultured at 37° C. The liquid was drained at a specific time point, and a mass of the remaining gel was weighed. The degradation curves are shown in FIG. 4, and the degradation experimental results show that the gel itself has a certain stability and is degradable under simulated in vivo conditions with trypsin and normal saline (chloride ions), which proves that the gel is biodegradable and has a certain chloride ion response, thus being beneficial for biomedical applications.

Figure 5:
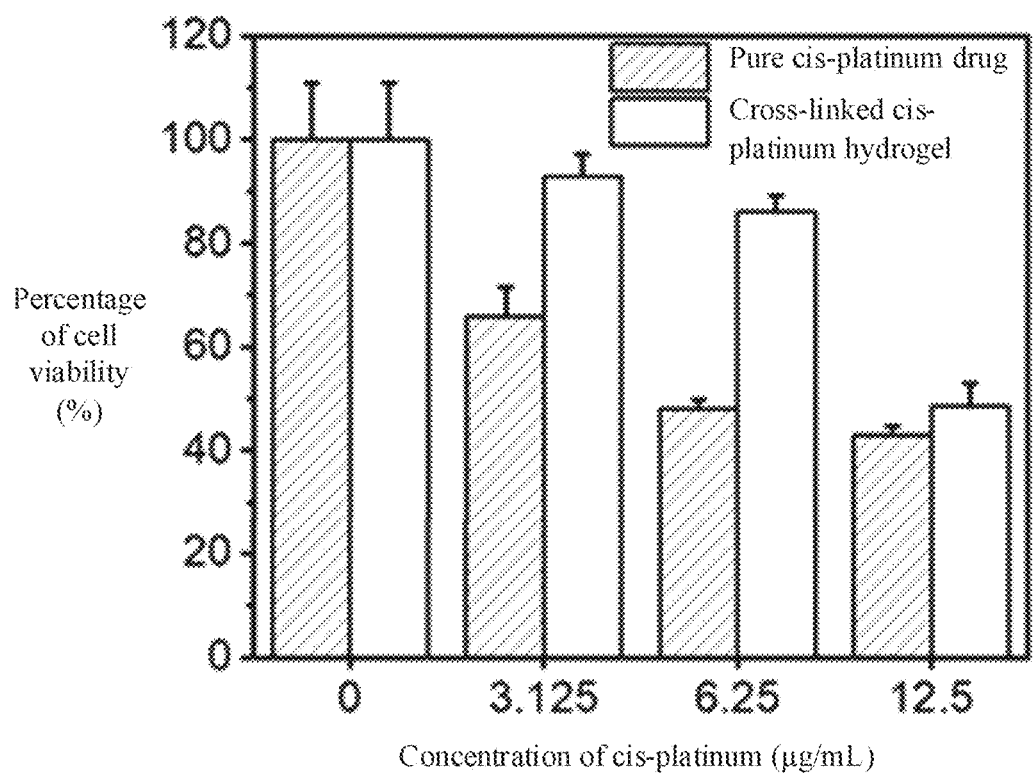
FIG. 5 shows a cytotoxicity experimental result of the cis-platinum cross-linked protein hydrogel obtained in Embodiment 2.

The cis-platinum cross-linked albumin hydrogel prepared in Embodiment 2 of the present invention was accurately weighed to obtain block gels loaded with different masses of cis-platinum, and corresponding pure cis-platinum solutions with different concentrations were prepared with a culture medium. Taking a 4T1 cell line as an object of study, cells were incubated in a 12-well plate at 30,000 cells/well overnight. A cytotoxicity study was carried out on the pure cis-platinum drug (pure cis-platinum drug in FIG. 5) and the cis-platinum cross-linked albumin hydrogel (cross-linked cis-platinum hydrogel in FIG. 5) obtained in Embodiment 2. It can be seen from the experimental results that the cis-platinum cross-linked albumin hydrogel obtained in Embodiment 2 has lower toxicity, which indicates that an effect between the cis-platinum and carboxyl slows down the release of the drug, thus showing a sustained release behavior. Therefore, a foundation is laid for reducing drug burst release and realizing sustained drug release.

Embodiment 3

60 mg of bovine serum albumin powder was added to 940 μL of ultrapure water and heated in a water bath at 65° C. for complete dissolution to obtain a clear light yellow solution. 10 mg of cis-platinum was added to the solution and placed on a shaking table, wherein the temperature was set to 37° C. and the rotating speed was set to 200 r/min, or the cis-platinum was evenly dispersed in the solution by mechanical stirring. After reaction for 72 hours to 84 hours, a protein hydrogel with cis-platinum as a cross-linking agent was obtained.

Embodiment 4

50 mg of bovine serum albumin powder was added to 50 μL of ultrapure water and heated in a water bath at 65° C. for complete dissolution to obtain a clear light yellow solution. 5 mg of cis-platinum was added to the solution and placed on a shaking table, wherein the temperature was set to 42° C. and the rotating speed was set to 10 r/min, or the cis-platinum was evenly dispersed in the solution by mechanical stirring. After reaction for 72 hours to 84 hours, a protein hydrogel with cis-platinum as a cross-linking agent was obtained.

Embodiment 5

20 mg of human serum albumin powder was added to 80 μL of ultrapure water and heated in a water bath at 25° C. for complete dissolution to obtain a clear light yellow solution. A total of 1.5 mg of cis-platinum was added to the solution and placed on a shaking table, wherein the temperature was set to 40° C. and the rotating speed was set to 230 r/min, or the cis-platinum was evenly dispersed in the solution by mechanical stirring. After reaction for 36 hours to 48 hours, a protein hydrogel with cis-platinum as a cross-linking agent was obtained.

Embodiment 6

30 mg of mouse serum albumin powder was added to 70 μL of ultrapure water and heated in a water bath at 45° C. for complete dissolution to obtain a clear light yellow solution. A total of 1.5 mg of cis-platinum was added to the solution and placed on a shaking table, wherein the temperature was set to 25° C. and the rotating speed was set to 230 r/min, or the cis-platinum was evenly dispersed in the solution by mechanical stirring. After reaction for 72 hours to 84 hours, a protein hydrogel with cis-platinum as a cross-linking agent was obtained.

Embodiment 7

500 mg of bovine serum albumin powder was added to 500 μL of ultrapure water and heated in a water bath at 25° C. for complete dissolution to obtain a clear light yellow solution. 6 mg of cis-platinum was added to the solution and placed on a shaking table, wherein the temperature was set to 65° C. and the rotating speed was set to 200 r/min, or the cis-platinum was evenly dispersed in the solution by mechanical stirring. After reaction for 48 hours to 72 hours, a protein hydrogel with cis-platinum as a cross-linking agent was obtained.

Embodiment 8

100 mg of bovine serum albumin powder was added to 900 μL of ultrapure water and heated in a water bath at 25° C. for complete dissolution to obtain a clear light yellow solution. 50 mg of cis-platinum was added to the solution and placed on a shaking table, wherein the temperature was set to 4° C. and the rotating speed was set to 230 r/min, or the cis-platinum was evenly dispersed in the solution by mechanical stirring. After reaction for 72 hours to 84 hours, a protein hydrogel with cis-platinum as a cross-linking agent was obtained.

The above embodiments are not intended to restrict the present invention, the present invention is not merely limited to the above embodiments, and so long as it meets the requirements of the present invention, it belongs to the scope of protection of the present invention.

We claim:

1. A cis-platinum cross-linked protein hydrogel, wherein main components of the cis-platinum cross-linked protein hydrogel comprise the following ingredients in percentage by mass: 0.5% to 5.0% drug, 6.0% to 50.0% serum albumin and 47.0% to 93.0% solvent medium; a carboxyl group on a surface of the serum albumin and the drug form a coordinate bond; and the drug is cis-platinum; the solvent medium is water or a solution without chloride ions;

the cis-platinum cross-linked protein hydrogel preparation is prepared by the following steps:

step (1): preparing the serum albumin and the solvent medium into a serum albumin solution, and heating the solution in a water bath until albumin is completely dissolved to obtain a clear albumin solution, and a temperature of the water bath is 25° C. to 65° C.; and step (2): adding the drug to the clear albumin solution above a colloid with fluidity was poured from a container into a mold with a bottom diameter of 2.5 cm when the drug completely disappeared, and put the mold into a shaking table at a constant temperature of 4° C. to 65° C. under a rotating speed of 10 r/min to 230 r/min for 36 hours to 84 hours to obtain the cis-platinum cross-linked protein hydrogel.

2. The cis-platinum cross-linked protein hydrogel according to claim 1, wherein the serum albumin is one of human serum albumin, bovine serum albumin and mouse serum albumin.

3. The cis-platinum cross-linked protein hydrogel according to claim 1, wherein the percentage by mass of the serum albumin is 15.0% to 40.0%.

4. The cis-platinum cross-linked protein hydrogel according to claim 3, wherein the percentage by mass of the serum albumin is 20.0% to 30.0%.

5. The cis-platinum cross-linked protein hydrogel according to claim 1, wherein the percentage by mass of the drug is 1.5% to 2.0%.

6. A cis-platinum cross-linked protein hydrogel, wherein main components of the cis-platinum cross-linked protein hydrogel comprise the following ingredients in percentage by mass: 0.5% to 5.0% drug, 6.0% to 50.0% serum albumin and 47.0% to 93.0% solvent medium; a carboxyl group on a surface of the serum albumin and the drug form a coordinate bond; and the drug is cis-platinum; the solvent medium is water or a solution without chloride ions;

the cis-platinum cross-linked protein hydrogel preparation is prepared by the following steps:

step (1): preparing the serum albumin and the solvent medium into a serum albumin solution, and heating the solution in a water bath until albumin is completely dissolved to obtain a clear albumin solution, and a temperature of the water bath is 25° C. to 65° C.; and step (2): adding the drug to the clear albumin solution above a colloid with fluidity was poured from a container into a mold with a bottom diameter of 2.5 cm when the drug completely disappeared, and put the mold into a shaking table at a constant temperature of 4° C. to 65° C. under a rotating speed of 10 r/min to 230 r/min for 36 hours to 84 hours to obtain the cis-platinum cross-linked protein hydrogel.

\* \* \* \* \*